United States Patent [19]

Schlosser et al.

[11] Patent Number: 5,445,763

[45] Date of Patent: Aug. 29, 1995

[54] 3-FLUOROPYRIDINES, PROCESS FOR THEIR PREPARATION, AND THEIR USE IN LIQUID-CRYSTAL MIXTURES

[75] Inventors: Hubert Schlosser, Glashuetten/Taunus; Anke Kaltbeitzel, Ruesselsheim, both of Germany

[73] Assignee: Hoechst Aktiengesellschaft, Frankfurt am Main, Germany

[21] Appl. No.: 72,929

[22] Filed: Jun. 7, 1993

[30] Foreign Application Priority Data

Jun. 9, 1992 [DE] Germany ............... 42 18 873.3

[51] Int. Cl.$^6$ ............... C09K 19/34; C07D 213/61; G02F 1/13
[52] U.S. Cl. ............... 252/299.61; 252/299.01; 252/299.62; 252/299.63; 252/299.67; 546/257; 546/303; 546/345; 359/103
[58] Field of Search ............... 252/299.01, 299.61, 252/299.62, 299.63; 546/303, 250, 257, 268, 303, 345

[56] References Cited

U.S. PATENT DOCUMENTS

| | | | |
|---|---|---|---|
| 4,684,734 | 8/1987 | Kaieda et al. | 546/304 |
| 5,204,471 | 4/1993 | Reiffenrath et al. | 546/303 |
| 5,205,962 | 4/1993 | Coates et al. | 252/299.61 |

FOREIGN PATENT DOCUMENTS

| | | |
|---|---|---|
| 0206228A3 | 12/1986 | European Pat. Off. . |
| 0284093 | 9/1988 | European Pat. Off. . |
| 0475444A1 | 3/1992 | European Pat. Off. . |
| 2169537 | 6/1990 | Japan . |
| WO91/04248 | 4/1991 | WIPO . |
| WO91/04249 | 4/1991 | WIPO . |
| WO92/09576 | 6/1992 | WIPO . |
| WO92/11241 | 7/1992 | WIPO . |

*Primary Examiner*—Shean Wu
*Attorney, Agent, or Firm*—Curtis, Morris & Safford

[57] ABSTRACT

A 3-fluoropyridine of the formula (I)

in which the symbols have the following meanings:
$R^1$ and $R^2$, independently of one another, are, for example, H or straight-chain or branched alkyl, $A^1$, $A^2$, $A^3$ and $A^4$ are identical or different and are, for example, 1,4-phenylene, pyrazine-2,5-diyl or trans-1,4-cyclohexylene, $M^1$, $M^2$, $M^3$ and $M^4$ are identical or different and are, for example, —O— or —CO—O—, $R^3$, $R^4$, $R^6$ and $R^7$, independently of one another are, for example, H or straight-chain or branched alkyl, $M^5$ is for example, —O—CO— or a single bond, k, l, m, n, o, p, q and r are zero or one, with the proviso that the sum $k+m+p+r$ is less than 4 and greater than zero, can advantageously be employed as a component in ferroelectric liquid-crystal mixtures.

8 Claims, No Drawings

3-FLUOROPYRIDINES, PROCESS FOR THEIR PREPARATION, AND THEIR USE IN LIQUID-CRYSTAL MIXTURES

The unusual combination of anisotropic and fluid behavior of liquid crystals has resulted in their use in electrical-optical switching and display devices, where their electrical, magnetic, elastic and/or thermal properties can be utilized to effect changes in alignment. Optical effects can be achieved, for example, with the aid of birefringence, the inclusion of dye molecules which absorb dichroically ("guest-host mode") or by light scattering.

In order to satisfy the constantly increasing practical requirements in the various areas of application, there is a constant demand for novel improved liquid-crystal mixtures and thus also for a wide range of mesogenic compounds of various structure. This applies both to areas in which nematic LC phases are used and to those in which smectic LC phases are used.

There has been particular interest recently in ferroelectric liquid-crystalline mixtures (FLC mixtures) (see, for example, J. W. Goodby, Ferroelectric Liquid Crystals, Gordon and Breach, Philadelphia, 1991). For practical use of ferroelectric liquid crystals in electro-optical displays, chiral, tilted, smectic phases, such as $S_c^*$ phases are required [see, for example, R. B. Meyer, L. Liebert, L. Strzelecki and P. Keller, J. Physique 36, L-69 (1975)], which are stable over a broad temperature range. This aim can be achieved by means of compounds which themselves form such phases, for example $S_c^*$ phases, or by doping compounds which do not form chiral, tilted, smectic phases with optically active compounds [see, for example, M. Brunet, C. Williams, Ann. Phys. 3, 237 (1978)].

When ferroelectric liquid-crystal mixtures are used in electro-optical components, a uniform planar alignment of the liquid crystals is necessary in order to achieve a high contrast ratio. It has been found that a uniform planar alignment in the $S_c^*$ phase can be achieved if the phase sequence of the liquid-crystal mixture is, with increasing temperature: isotropic-nematic→smectic A-smectic C (see, for example, K. Flatischler et al., Mol. Cryst. Liq. Cryst. 131, 21 (1985); T. Matsumoto et al., p.468–470, Proc. of the 6th Int. Display Research Conf., Japan Display, 30 Sep. -2 Oct. 1986, Tokyo, Japan; M. Murakami et al., ibid, p. 344–347).

For ferroelectric (chiral smectic) liquid-crystal mixtures, the condition must additionally be satisfied that the pitch of the helix in the $S_c$ * phase is large, i.e. greater than 5 μm, and the pitch of the helix in the N* phase is very large, i.e. greater than 10 μm, or is infinite.

The optical response time $\tau[\mu s]$ of ferroelectric liquid-crystal systems, which should be as short as possible, depends on the rotational viscosity of the system $\gamma$[mPas], the spontaneous polarization $P_s$[nC/cm$^2$] and the electrical field strength E[V/m], in accordance with the equation $$\tau \approx \frac{\gamma}{P_S \cdot E}$$

Since the field strength E is determined by the electrode separation in the electro-optical component and by the applied voltage, the ferroelectric display medium must have low viscosity and high spontaneous polarization in order to achieve a short response time.

Finally, in addition to thermal, chemical and photochemical stability, a small optical anisotropy Δn, preferably ≃0.13, and a low positive or preferably negative dielectric anisotropy Δε are required (see, for example, S. T. Lagerwall et al., "Ferroelectric Liquid Crystals for Displays" SID Symposium, October Meeting 1985, San Diego, Calif., USA).

The totality of these requirements can generally only be satisfied by means of mixtures comprising a plurality of components. As the base (or matrix), preference is given to compounds which themselves already have the desired phase sequence I→N→$S_A$→$S_c$. Further components of the mixture are frequently added in order to reduce the melting point and to broaden the $S_c$ phase and usually also the N phase, to induce optical activity, for pitch compensation and to match the optical and dielectric anisotropy; however, the rotational viscosity, for example, should if possible not be increased.

Some of these components and also certain mixtures are already known from the prior art. However, since development in particular of ferroelectric liquid-crystal mixtures, can in no way be regarded as complete, the manufacturers of displays are interested in various mixtures. This is also the case because, inter alia, only the interaction of the liquid-crystalline mixtures with the individual components of the display devices or of the cells (for example the alignment layer) allows conclusions to be made on the quality of the liquid-crystalline mixtures also.

EP-A 0 158 137 describes 4-fluoropyrimidines as compounds and as mixture components in general. However, they only have a slight tendency, or none at all, to form smectic phases and are therefore used in nematic mixtures.

DE-A 40 29 165 and DE-A 40 30 582 present 4-fluoropyrimidines as components of ferroelectric liquid-crystal mixtures.

It is furthermore known that mono- and difluorophenyl compounds can be used as components of liquid-crystal mixtures (see, for example, JP-A 2169-537; V. Reiffenrath, The Twelfth International Liquid Crystal Conference, Freiburg, 15–19 Aug. 1988). However, some of these compounds do not have an $S_c$ phase. Furthermore, fluorophobic interactions frequently cause some miscibility problems with structurally different mixture components, for example phenyl pyrimidines.

Pyridine derivatives likewise have a liquid-crystalline behavior and form an $S_c$ phase (T. Geelhaar, 1st International Symposium on Ferroelectric Liquid Crystals, Arcachon, 2–23 Sep. 1987; U.S. Pat. No. 4,952,335). However, an $S_I$ phase which frequently occurs in these compounds impairs their use in ferroelectric liquid-crystal mixtures.

Derivatives of 2-fluoropyridine having exclusively nematic phases are described in WO-91/04249 and WO-91/04248 for use in liquid-crystal mixtures.

The present invention relates to 3-fluoropyridine derivatives of the formula (I) and to the use thereof as components of ferroelectric liquid-crystal mixtures, where at least one 3-fluoropyridine of the formula (I) is employed as a component in a liquid-crystal mixture.

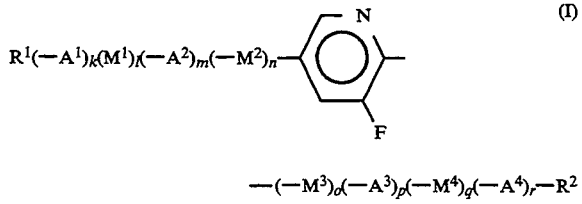

$$R^1(-A^1)_k(M^1)_l(-A^2)_m(-M^2)_n\text{—pyridine-F ring—} \tag{I}$$

$$-(-M^3)_o(-A^3)_p(-M^4)_q(-A^4)_r-R^2$$

The symbols in this formula have the following meanings:

$R^1$ and $R^2$, are identical or different and are —H, —F, —Cl, —CN, —NCS, —CF$_3$, —OCF$_3$, —OCHF$_2$ or straight-chain or branched (with or without an asymmetric carbon atom) alkyl having 1 to 16 or carbon atoms respectively, it also being possible for one or two non-adjacent —CH$_2$— groups to be replaced by

—O—, —S—, —CO—, —CO—O—, —O—CO—,
—CO—S—, —S—CO—, —O—CO—O—,

—CH=CH—, —C≡C—, cyclopropyl or —Si(CH$_3$)$_2$—, and it also being possible for one or more hydrogen atoms in the alkyl radical to be substituted by —F, —Cl, —Br or —CN, or are one of the following chiral groups:

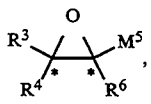 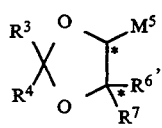

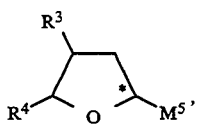 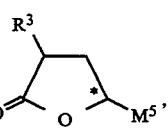

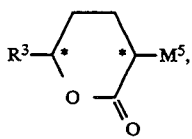 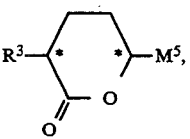

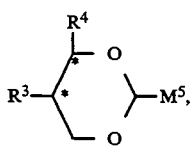 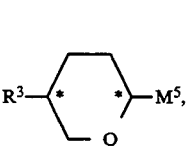

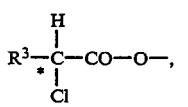 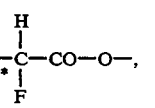

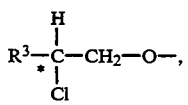 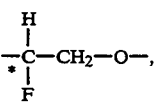

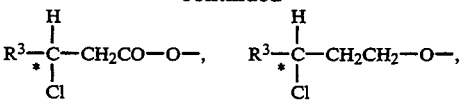 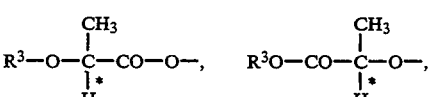

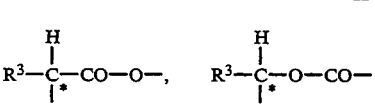

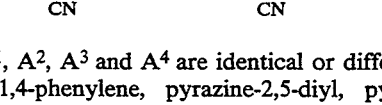

$A^1$, $A^2$, $A^3$ and $A^4$ are identical or different and are 1,4-phenylene, pyrazine-2,5-diyl, pyridazine-3,6-diyl, pyridine-2,5-diyl, pyrimidine-2,5-diyl, where one or two hydrogen atoms may be replaced by F, trans-1,4-cyclohexylene, in which one or two hydrogen atoms may in each case be replaced by CN, 1,3,4-thiadiazole-2,5-diyl, 1,3-dioxane-2,5-diyl, naphthalene-2,6-diyl, bicyclo[2.2.2.]octane-1,4-diyl or 1,3-dioxaborinane-2,5-diyl;

$M^1$, $M^2$, $M^3$ and $M^4$ are identical or different and are —O—, —S—, —CO—, —CO—O—, —O—CO—, —CO—S—, —S—CO—, —O—CO—O—, —CH$_2$—O—, —O—CH$_2$—, —CH$_2$—CH$_2$—, —CH=CH— or —C≡C—;

$R^3$, $R^4$, $R^6$ and $R^7$ are identical or different and are H or straight-chain or branched alkyl having 1 to 16 carbon atoms respectively, or $R^3$ and $R^4$ together are alternatively —(CH$_2$)$_4$— or —(CH$_2$)$_5$— if bonded as substituents to a dioxolane system;

$M^5$ is —CH$_2$—O—, —CO—O—, —O—CH$_2$—, —O—CO— or a single bond;

k, l, m, n, o, p, q and r are zero or one, with the proviso that the sum k+m+p+r is less than 4 and greater than zero.

In a preferred embodiment of the invention, the symbols in the formula (I) have the following meanings:

$R^1$ and $R^2$ are identical or different and are —H, —F, —CN or straight-chain or branched (with or without an asymmetric carbon atom) alkyl having 1 to 16 carbon atoms respectively, it also being possible for one —CH$_2$— group to be replaced by

—O—, —S—, —CO—, —CO—O—, —O—CO—,
—O—CO—O—, —CH=CH—, —C≡C—,

 or —Si(CH$_3$)$_2$—, or are one of the following chiral groups:

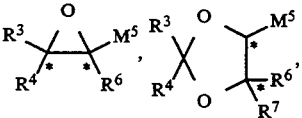 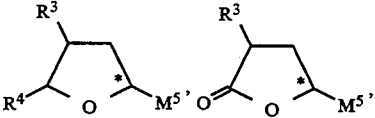

-continued

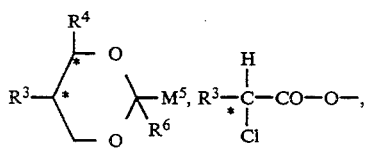

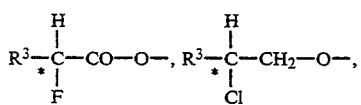

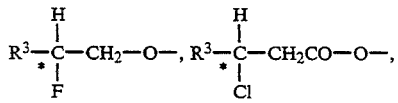

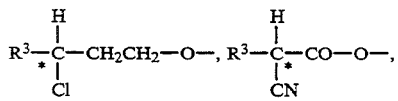

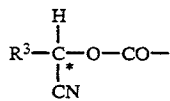

$A^1$, $A^2$, $A^3$ and $A^4$ are identical or different and are 1,4-phenylene, pyrazine-2,5-diyl, pyridazine-3,6-diyl, pyridine-2,5-diyl, pyrimidine-2,5-diyl, in which one or two hydrogen atoms may in each case be replaced by F, trans-1,4-cyclohexylene, 1,3,4-thiadiazole-2,5-diyl, 1,3-dioxane-2,5-diyl, naphthalene-2,6-diyl, bicyclo[2.2.2]octane-1,4-diyl or 1,3-dioxaborinane-2,5-diyl;

$M^1$, $M^2$, $M^3$ and $M^4$ are identical or different and are —O—, —CO—, —CO—O—, —O—CO—, —CH$_2$—O—, —O—CH$_2$—, —CH$_2$—CH$_2$—, —CH=CH— or —C≡C—;

$R^3$, $R^4$, $R^6$ and $R^7$ are identical or different and are H or straight-chain or branched alkyl having 1 to 10 or 3 to 10 carbon atoms respectively, or $R^3$ and $R^4$ together are alternatively —(CH$_2$)$_4$— or —(CH$_2$)$_5$— if bonded as substituents to a dioxolane system;

$M^5$ is —CH$_2$—O—, —CO—O—, —O—CH$_2$—, —O—CO— or a single bond.

Preference is furthermore given to 3-fluoropyridine derivatives of the formula (I) in which the symbols have the following meanings:

$R^1$ and $R^2$ are identical or different and are —H, —F, —CN or straight-chain or branched (with or without an asymmetric carbon atom) alkyl having 1 to 6 carbon atoms respectively, it also being possible for one —CH$_2$— group to be replaced by —O—, —CO—, —CO—O—, —O—CO—, —CH=CH— or —Si(CH$_3$)$_2$—, or are one of the following chiral groups:

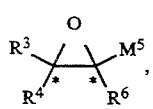 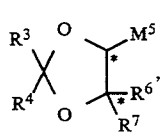

-continued

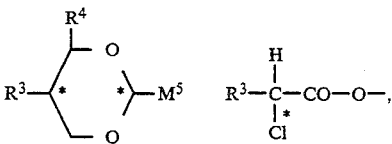

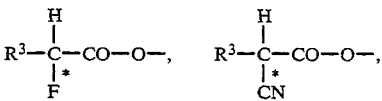

$A^1$, $A^2$, $A^3$ and $A^4$ are identical or different and are 1,4-phenylene, pyrazine-2,5-diyl, pyridazine-3,6-diyl, pyridine-2,5-diyl, pyrimidine-2,5-diyl, in which one or two hydrogen atoms may be replaced by F, trans-1,4-cyclohexylene, 1,3-dioxane-2,5-diyl, naphthalene-2,6-diyl or 1,3-dioxaborinane-2,5-diyl;

$M^1$, $M^2$, $M^3$ and $M^4$ are identical or different and are —O—, —CO—O—, —O—CO—, —O—CH$_2$—, —CH$_2$—O—, —CH$_2$—CH$_2$— or —CH=CH—;

$R^3$, $R^4$, $R^6$ and $R^7$ are identical or different and are H or straight-chain or branched alkyl having 1 to 10 carbon atoms, or $R^3$ and $R^4$ together are alternatively —(CH$_2$)$_4$— or —(CH$_2$)$_5$— if bonded as substituents to a dioxolane system;

$M^5$ is —CH$_2$—O—, —CO—O—, —O—CH$_2$—, —O—CO— or a single bond.

Particular preference is given to a 3-fluoropyridine of the formula (I) in which $R^1$ and $R^2$ are identical or different and are H or alkyl having 1 to 16 carbon atoms, it also being possible for one —CH$_2$— group to be replaced by —O—, —CO—O— or —O—CO—, or are the chiral group

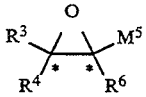

$A^1$, $A^2$, $A^3$ and $A^4$ are identical or different and are 1,4-phenylene, pyrazine-2,5-diyl, pyridazine-3,6-diyl, pyridine-2,5-diyl, pyrimidine-2,5-diyl, in which one or two hydrogen atoms may in each case be replaced by F, trans-1,4-cyclohexylene, 1,3-dioxane-2,5-diyl, naphthalene-2,6-diyl or 1,3-dioxaborinane-2,5-diyl;

$M^1$, $M^2$, $M^3$ and $M^4$ are identical or different and are —O—, —CO—O—, —O—CO—, —OCH$_2$—, —CH$_2$—O— or —CH$_2$CH$_2$—;

$R^3$, $R^4$ and $R^6$ are identical or different and are H or straight-chain alkyl having 1 to 10 carbon atoms;

$M^5$ is —CH$_2$—O— or —CO—O—.

The compounds according to the invention are chemically and photochemically stable. They have low melting points and generally have broad liquid-crystalline phases, in particular broad nematic, smectic A and smectic C phases.

Furthermore, the compounds according to the invention are distinguished by increased miscibility, low viscosity and $\Delta\varepsilon$ values which are close to zero.

Liquid-crystalline compounds containing this structural element can be used to prepare both ferroelectric mixtures and nematic or chiral nematic mixtures which are suitable for use in electro-optical or fully optical elements, for example display elements, switching elements, light modulators, elements for image processing, signal processing or generally in the area of non-linear optics.

The liquid-crystal mixtures according to the invention generally comprise 2 to 20, preferably 2 to 15, components, including at least one compound of the formula (I). The other constituents are preferably selected from known compounds having nematic, cholesteric and/or tilted smectic phases; these include, for example, Schiff bases, biphenyls, pyridines, thiadiazoles, difluorophenyls, terphenyls, phenylcyclohexanes, cyclohexylbiphenyls, pyrimidines, cinnamic acid esters, cholesterol esters and polycyclic esters of p-alkylbenzoic acids. In general, the commercially available liquid-crystal mixtures are already, before addition of the compound(s) according to the invention, in the form of mixtures of the various components, of which at least one is mesogenic.

The liquid-crystal mixtures generally contain from 0.1 to 70 mol %, preferably from 0.5 to 50 mol %, in particular from 1 to 25 mol %, of the 3-fluoropyridine derivative(s) according to the invention.

The values for the spontaneous polarization $P_s$[nC/cm$^2$], the contrast C and the optical response time $\tau$[µs] were determined for the ready-to-use ferroelectric liquid-crystal mixtures, all measurements being carried out at a temperature of 25° C.

The $P_s$ values are measured by the method of H. Diamant et al. (Rev. Sci. Instr., 28, 30, 1957), using measurement cells having an electrode separation of 2 µm and rubbed polyimide as alignment layer. In order to determine $\tau$ and C, the measurement cell is mounted between crossed analyzer and polarizer on the rotary stage of a polarizing microscope. For determining the contrast (C), the measurement cell was positioned by rotation so that a photodiode indicates minimum light transmission (dark state). The microscope illumination is adjusted so that the photodiode indicates the same light intensity for all cells. After a switching operation, the light intensity changes (bright state) and the contrast is calculated from the ratio between the light intensities in these states.

In order to determine $\tau$ and the switching angle $\phi_{eff}$, the position of the stage at which light transmission is at its lowest is determined for the two switching states in the cell by rotating the stage. The difference between the two positions on the rotary stage is equal to twice the effective tilt angle. With the aid of a photodiode, the response time $\tau$ is determined by measuring the time taken for the light signal to increase from 10 to 90%. The switching voltage comprises rectangular pulses and is ±10 V/µm.

The phase transition temperatures are determined with the aid of a polarizing microscope from the changes in texture during heating. By contrast, the melting point was determined using a DSC instrument. The phase transition temperatures between the phases

| nematic | (N or N*) |
| smectic C | (S$_C$ or S$_C$*) |
| smectic A | (S$_A$ or S$_A$*) |
| crystalline | (X) | are given in °C. and the values are between the phase designations in the phase sequence.

Liquid-crystalline mixtures which contain compounds of the formula (I) are particularly suitable for use in electro-optical switching and display devices (displays). Switching and display devices (LC displays) contain, inter alia, the following constituents: a liquid-crystalline medium, outer plates (for example made of glass or plastic), coated with transparent electrodes, at least one alignment layer, spacers, an adhesive frame, polarizers and, for color displays, thin colored filter layers. Further possible components are antireflection, passivation, equalization and barrier layers and electrically non-linear elements, such as thin-film transistors (TFTs) and metal/insulator/metal (MIM) elements. The structure of liquid-crystal displays has already been described in detail in relevant monographs (for example E. Kaneko, "Liquid Crystal TV Displays: Principles and Applications of Liquid Crystal Displays", KTK Scientific Publishers, 1987, pages 12–30 and 63–172).

The compounds according to the invention can be prepared, for example, by the process outlined in schemes 1 to 6, in which the side chains $R^1(-A^1)_k(-M^1)_l(-A^2)_m(-M^2)_n$- and $(-M^3)_o(-A^3)_p(-M^4)_q(A^4)_r$- $R^2$ are introduced into the 2- or 5-position of the pyridine ring by a multistep reaction via the intermediate 2,5-dibromo-3-fluoropyridine (VI).

The starting compound in the preparation process according to the invention is 2-amino-5-bromopyridine (II), which is commercially available and can be converted into 5-bromo-2-hydroxy-3-nitropyridine (III) by means of nitric and sulfuric acid analogously to the method described by T. S. Safonova and L. G. Levkovskaya in Khim. Geterotsikl. Soedin 1968, pages 997–1000.

Reaction of the 2-hydroxypyridine (III) with a brominating agent, such as phosphorus tribromide, phosphorus oxytribromide and phosphorus pentabromide, at temperatures between 50° and 200° C., in particular between 100° and 150° C. gives 2,5-dibromo-3-nitropyridine (IV), which is reduced to 3-amino-2,5-dibromopyridine (V) by methods known per se from the literature (see, for example, Houben-Weyl, Methoden der Organischen Chemie [Methods of Organic Chemistry], George Thieme Verlag, Stuttgart).

The compound (V) can be converted into 2,5-dibromo-3-fluoropyridine (VI) by the method of Balz and Schiemann (see Houben-Weyl, Methoden der Organischen Chemie [Methods of Organic Chemistry], George Thieme Verlag, Stuttgart) by diazotization to give the diazonium tetrafluoroborate and thermal decomposition thereof.

An alternative starting compound in the preparation process according to the invention is 3-fluoro-2-hydroxypyridine (XIV), which can be prepared by the method described by M. P. Cava and B. Weinstein in Journal of Organic Chemistry 23 (1958) on pages 1616 to 1617.

Reaction of 3-fluoro-2-hydroxypyridine (XIV) with bromine at temperatures between −70° C. and 150° C., in particular between −20° C. and 50° C., in an inert solvent gives 5-bromo-3-fluoro-2-hydroxypyridine (XV), which can be converted into 2,5-dibromo-3-fluoropyridine (VI) by treatment with a brominating agent, such as phosphorus tribromide, phosphorus oxytribromide and phosphorus pentabromide, at temperatures between 50° C. and 250° C., in particular between 100° C. and 170° C.

Replacement of the bromine substituent in the 2-position of compound (VI) by a group of the formula $Z^1=(-M^3)_o(-A^3)_p(-M^4)_q(-A^4)_r-R^2$ by reaction with a metal compound of $Z^1$, for example a lithium, sodium, potassium or magnesium compound, at temperatures between −40° and 100° C., in particular between −10° and 70° C., in an inert reaction medium, for example diethyl ether, tetrahydrofuran, 1,4-dioxane, ethylene glycol diethyl ether or diethylene glycol diethyl ether, gives compounds of the formula (VII).

Cross-coupling of compound (VI) with organometallic derivatives of $Z^1$, for example Grignard, lithium and zinc derivatives, and boronic acids of $Z^1$ using transition-metal catalysts, for example [1,3-bis(diphenylphosphino)propane]nickel(II) chloride and tetrakis(triphenylphosphine)palladium(0), at temperatures between −40° and 200° C. in particular between −10° and 100° C., in reaction media such as benzene/ethanol/water for reaction with boronic acids of $Z^1$ and, for example, diethyl ether or tetrahydrofuran for the reaction with Grignard, lithium and zinc derivatives of $Z^1$ likewise gives compounds of the type (VII).

Cross-coupling of compounds of type (VII) with organometallic derivatives of $Z^2$, for example Grignard, lithium and zinc derivatives, and boronic acids of $Z^2$ using transition-metal catalysts, for example [1,3-bis(diphenylphosphino)propane]nickel(II) chloride and tetrakis(triphenylphosphine)palladium(0) at temperatures between −40° and 200° C., in particular between −10° and 100° C., in reaction media such as benzene/ethanol/water for the reaction with boronic acids of $Z^2$ and diethyl ether or tetrahydrofuran for the reaction with Grignard, lithium and zinc derivatives of $Z^2$ gives 3-fluoropyridines (I).

3-fluoropyridines of type (VII) can be converted into 3-fluoro-5-1-lithiopyridines of the formula (VIII) by treatment with an alkyllithium compound, such as n-butyllithium, tert-butyllithium or methyllithium, at temperatures between −100° and 50° C. in particular between −80° and 10° C. in an inert reaction medium, for example diethyl ether, tetrahydrofuran or ethylene glycol dimethyl ether. 5-lithiopyridines of the formula (VIII) are capable of undergoing reaction with electrophilic compounds, which gives 3-fluoropyridines of the formula (I), either directly or via further intermediates (compounds (IX), (X), (XI), (XII) and (XIII)).

Thus, 3-fluoro-5-lithiopyridines (VIII) give 3-fluoro-5-pyridinecarboxylic acids of the formula (IX) after treatment with carbon dioxide at temperatures between −100° and 50° C. in particular between −80° and 10° C. in an inert reaction medium, for example diethyl ether, tetrahydrofuran or ethylene glycol diethyl ether. Species (IX) can be converted into compounds of the formula (I) by methods known per se from the literature (see, for example, Houben-Weyl, Methoden der Organischen Chemie [Methods of Organic Chemistry], Georg Thieme Verlag, Stuttgart), either directly by esterification using alcohols of $Z^3$ with the aid of suitable condensation agents, for example carbodiimides, to give 3-fluoropyridines (I), or, after reduction to 3-fluoro-5-hydroxymethylpyridines (X) by means of suitable reducing agents, for example complex hydrides, by esterification with carboxylic acids or carboxylic halides of $Z^3$ or by etherification by means of alcohols or halides of $Z^3$.

The reaction of compounds of type (VIII) with nitriles, carboxylic halides and formylmethyl derivatives of $Z^3$ at temperatures between −100° and 50° C., in particular between −80° and 10° C., in an inert reaction medium, for example diethyl ether, tetrahydrofuran or ethylene glycol diethyl ether, results directly in 3-fluoropyridines of the formula (I). Olefinic 3-fluoropyridines (I) can be converted into saturated species (I) by hydrogenation of the olefinic double bond by methods known per se from the literature (see, for example, Houben-Weyl, Methoden der Organischen Chemie [Methods of Organic Chemistry], Georg Thieme Verlag, Stuttgart).

Reaction of 3-fluoro-5-lithiopyridines (VIII) with formamides at temperatures between −100° and 50° C., in particular between −80° and 10° C., in an inert reaction medium, for example diethyl ether, tetrahydrofuran or ethylene glycol diethyl ether, gives 3-fluoro-5-formylpyridines (XI), which give 3-fluoropyridines of type (I) after acid-catalyzed acetalization using 2-$Z^4$-1,3-propanediols by methods known per se from the literature (see, for example, Houben-Weyl, Methoden der Organischen Chemie [Methods of Organic Chemistry], Georg Thieme Verlag, Stuttgart).

Successive treatment of the 3-fluoro-lithiopyridine (VII) with trialkyl borates at temperatures between −100° and 50° C., in particular between −80° and 10° C., and aqueous acid at temperatures between −10° and 50° C., in particular between 10° and 30° C., in an inert reaction medium, for example diethyl ether, tetrahydrofuran or ethylene glycol diethyl ether, gives 3-fluoro-5-pyridineboronic acids of the formula (XII).

The boronic acids (XII) can be subjected to coupling reactions with halides of $Z^3$ using a transition-metal catalyst, for example tetrakis(triphenylphosphine)palladium(0), at temperatures between 30° and 200° C., in particular between 50° and 100° C., in reaction media such as benzene/ethanol/water, in order to prepare compounds of type (I).

3-fluoropyridines (I) are furthermore obtained from the boronic acids (XII) by esterification thereof using 2-$Z^4$-1,3-propanediols by methods known per se from the literature (see, for example, Houben-Weyl, Methoden der Organischen Chemie [Methods of Organic Chemistry], Georg Thieme Verlag, Stuttgart).

Oxidation of the boronic acids (XII) using peroxides, for example hydrogen peroxide, at temperatures between 10° and 100° C. in particular between 30° and 70° C., in reaction media such as, for example, diethyl ether or tetrahydrofuran, gives the 3-fluoro-5-hydroxypyridines (XIII), which can be converted into 3-fluoropyridines of the formula (I) by methods known per se from the literature (see, for example, Houben-Weyl, Methoden der Organischen Chemie [Methods of Organic Chemistry], Georg Thieme Verlag, Stuttgart) by esterification by means of carboxylic acids or carboxylic halides of $Z^3$ or by etherification by means of alcohols or halides of $Z^3$.

Scheme 1:

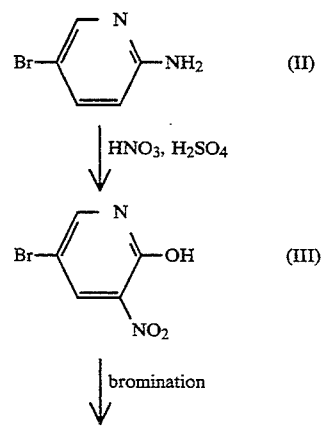

-continued
Scheme 1:
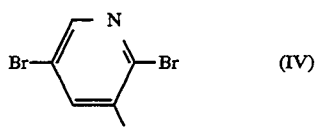 (IV)
↓ reduction
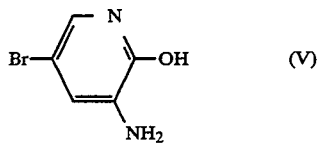 (V)
1. H⁺, NaNO₂, HBF₄
2. ΔT
↓
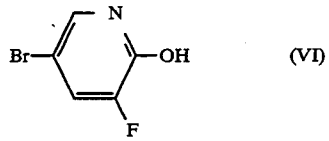 (VI)
Scheme 2:
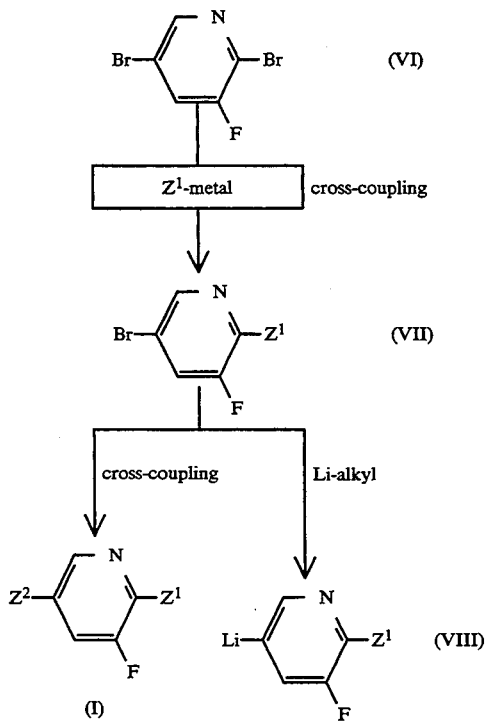
-continued
Scheme 2:
$Z^1 = (M^3)_o(-A^3)_p(-M^4)_q(-A^4)_r-R^2$
$Z^2 = R^1(-A^1)_k(-M^1)_l(-A^2)_m(-M^2)_n-$
Scheme 3:
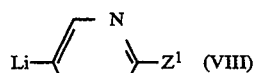 (VIII)
↓ CO₂
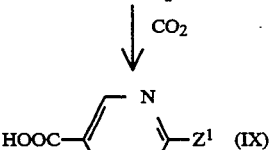 (IX)
↓ reduction
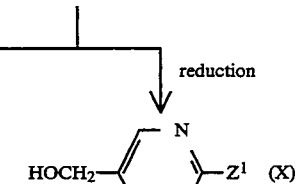 (X)
esterification using Z³—OH
esterification using Z³—COOH bzw. Z³—COX
or
etherification using Z³—OH bzw. Z³—X
↓
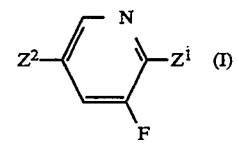 (I)
Z¹, Z² see Scheme 2
$Z^3 = R^1(-A^1)_k(-M^1)_l(-A^2)_m-$
X = Cl, Br, I Scheme 4:
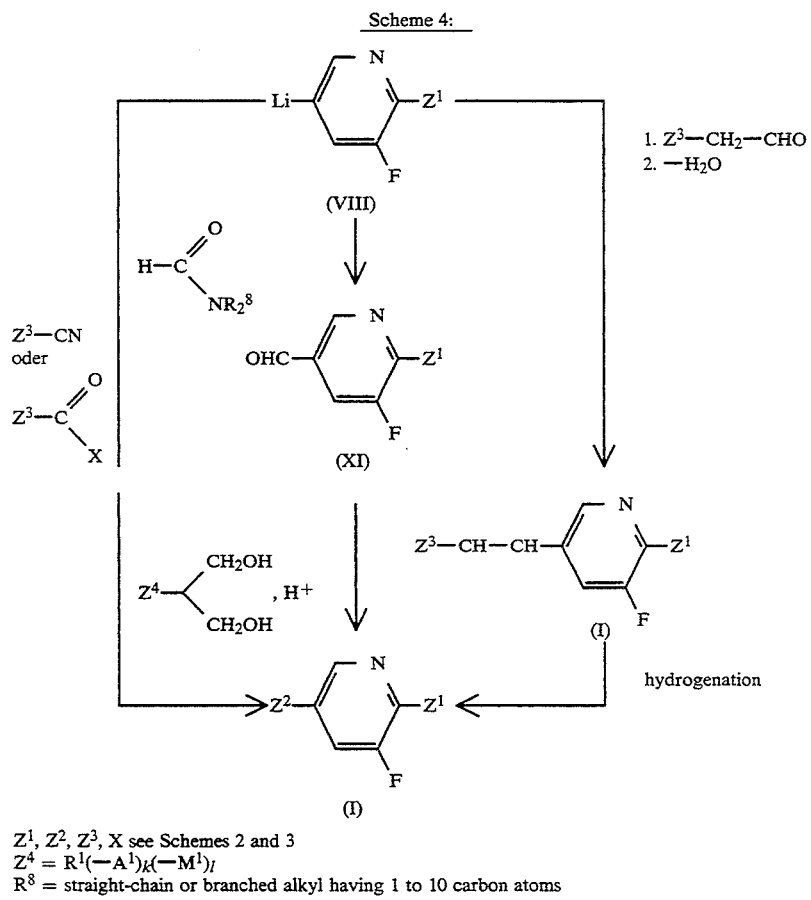
$Z^1$, $Z^2$, $Z^3$, X see Schemes 2 and 3
$Z^4 = R^1(-A^1)_k(-M^1)_l$
$R^8$ = straight-chain or branched alkyl having 1 to 10 carbon atoms
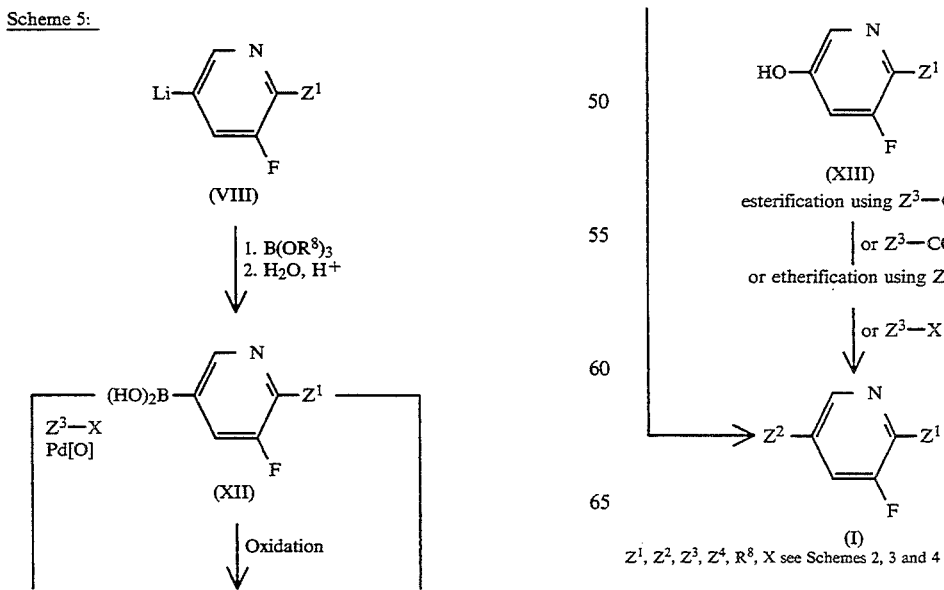

Scheme 6:

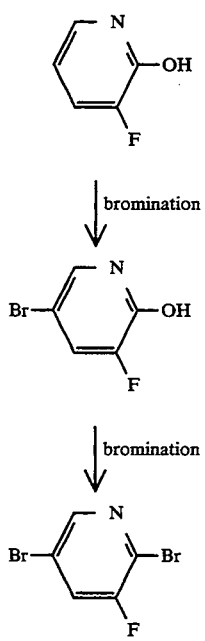

The invention is described in greater detail by means of the examples below:

EXAMPLE 1

3-fluoro-5-octyl-2-(4-octyloxyphenyl)pyridine 34.5 ml (821.6 mmol) of fuming nitric acid (d=1.5 g/cm$^3$) are added dropwise at 60° C. to 100 g (574.7 mmol) of 2-amino-5-bromopyridine in 300 ml of concentrated sulfuric acid (d=1.84 g/cm$^3$), and the mixture is subsequently stirred at 60° C. for 2 hours. The reaction mixture is poured into ice water, and the precipitated solid is filtered off, washed with water and dried, giving 88.16 g of 5-bromo-2-hydroxy-3-nitropyridine.

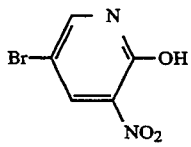

77.11 g (354.4 mmol) of 5-bromo-2-hydroxy-3-nitropyridine are heated at 120° C. for 3 hours together with 101.61 g (354.4 mmol) of phosphorus oxytribromide and 33.7 ml (354.4 mmol) of phosphorus tribromide. The reaction mixture is subsequently poured carefully, in small portions, into ice water, stirred for 1 hour and extracted three times with dichloromethane. The organic phase is washed twice with water, dried over sodium sulfate, filtered and freed from the solvent. Chromatographic purification (silica gel/dichloromethane) gives 43.05 g of 2,5-dibromo-3-nitropyridine.

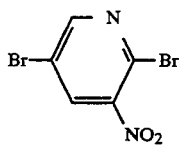

43.00 g (152.52 mol) of 2,5-dibromo-3-nitropyridine are hydrogenated in 1.5 g of Pd (10%) on activated charcoal in 450 ml of methanol until the calculated mount of hydrogen has been consumed, the catalyst is filtered off, and the filtrate is freed from solvent, giving 37.56 g of 3-amino-2,5-dibromopyridine.

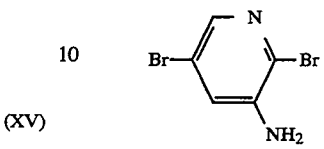

37.00 g (146.87 mmol) of 3-amino-2,5-dibromopyridine are diazotized in 50 ml of aqueous HBF$_4$ (35% strength) at −10° C. using 11.10 g (160.87 mmol) of sodium nitrite in 20 ml of water. After the reaction mixture has been stirred for a further half an hour at −10° C., it is heated at 50° C. for 30 minutes, poured into ice water, neutralized using sodium hydrogencarbonate and extracted three times with dichloromethane. The organic phase is washed twice with water, dried over sodium sulfate, filtered and freed from solvent. Chromatographic purification (silica gel/dichloromethane) gives 11.10 g of 2,5-dibromo-3-fluoropyridine.

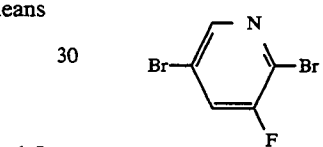

2.40 g (99.0 mmol) of magnesium and 25.56 g (89.6 mmol) of 4-octyloxybromobenzene in 250 ml of tetrahydrofuran are used to prepare, at 60° C. for 3 hours, the solution of the Grignard compound, which is added dropwise to a solution, cooled to −70° C., of 18.62 g (99.00 mmol) of triisopropyl borate in 100 ml of tetrahydrofuran, and the mixture is stirred overnight. 130 ml of 10% strength hydrochloric acid are subsequently added dropwise, the mixture is stirred at room temperature for 1 hour and partitioned between sodium chloride solution and ether, and the organic phase is washed with sodium chloride solution, dried over sodium sulfate and evaporated, giving 21.26 g of 4-octyloxybenzeneboronic acid.

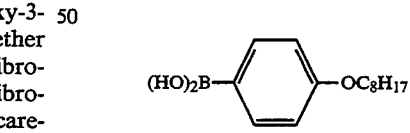

12.74 g (50.00 mmol) of 2,5-dibromo-3-fluoropyridine, 12.51 g (50.00 mmol) of 4-octyloxybenzeneboronic acid, 0.58 g (0.50 mmol) of tetrakis(triphenylphosphine)palladium(0) and 10.60 g (100 mmol) of sodium carbonate are heated at 80° C. for 3 hours in 375 ml of toluene, 250 ml of ethanol and 125 ml of water. The mixture is subsequently partitioned between aqueous sodium chloride solution and ether, and the organic phase is washed with aqueous sodium chloride solution, dried over sodium sulfate, evaporated and purified by chromatography (silica gel/hexane : ethyl acetate =9:1), giving 13.31 g of 5-bromo-3-fluoro-2-(4-octyloxyphenyl)pyridine.

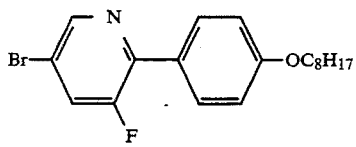

0.30 g (12.30 mmol) of magnesium and 2.16 g (11.18 mmol) of octyl bromide in 10 ml of tetrahydrofuran are used to prepare, at 50° C. for 2 hours, the solution of the Grignard compound, which is added dropwise to a solution, cooled to −10° C. of 2.13 g (5.59 mmol) of 5-bromo-3-fluoro-2-(4-octyloxyphenyl)pyridine and 0.03 g (0.06 mmol) of [1,3-bis(diphenylphosphino)-propane]nickel(II) chloride in 60 ml of tetrahydrofuran, and the mixture is stirred at −10° C. for 3 hours. The mixture is subsequently partitioned between ether and aqueous ammonium chloride solution, and the organic phase is washed twice with aqueous sodium chloride solution, dried over sodium sulfate and evaporated to dryness. Chromatographic purification (silica gel/dichloromethane:hexane 7:3) gives 1.89 g of 3-fluoro-5-octyl-2-(4-octyloxyphenyl)pyridine.

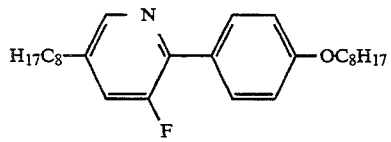

The compound has the phase sequence: X 25.5 (5) N 35 I.

EXAMPLE 2

3-fluoro-5-octyloxy-2-(4-octyloxyphenyl)pyridine 15 ml (24.00 mmol) of 1.6 molar n-butyllithium solution in hexane are added dropwise to a solution, cooled to −70° C., of 7.61 g (20.00 mmol) of 5-bromo-3-fluoro-2-(4-octyloxyphenyl)pyridine in 400 ml of tetrahydrofuran, and the mixture is stirred at −70° C. for 15 minutes. 7.5 g (40.00 mmol) of triisopropyl borate are subsequently added dropwise, the mixture is stirred at −70° C. for 1.5 hours and warmed to room temperature, 500 ml of ammonium chloride solution and 500 ml of ether are added, and the organic phase is separated off and washed twice with aqueous sodium chloride solution, dried over sodium sulfate and evaporated. The resultant 3-fluoro-2-(4-octyloxyphenyl)pyridine-5-boronic acid is refluxed for 2 hours in 100 ml of tetrahydrofuran with 30 ml of 17.5% strength by weight aqueous hydrogen peroxide solution and subsequently cooled to 0° C., and 200 ml of aqueous sodium sulfite solution are added dropwise. The organic phase is separated off, washed twice with aqueous sodium chloride solution, dried over sodium sulfate and evaporated to dryness. Recrystallization from 1,2-dichloroethane gives 5.08 g of 3-fluoro-5-hydroxy-2-(4-octyloxyphenyl)pyridine.

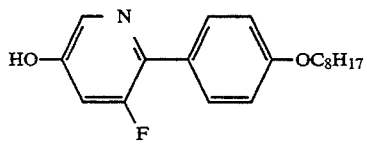

2.00 g (11.5 mmol) of diethyl azodicarboxylate are added dropwise at 0° C. to 3.00 g (11.5 mmol) of triphenylphosphine in 50 ml of tetrahydrofuran, and the mixture is stirred at room temperature for 30 minutes. 2.42 g (7.7 mmol) of 3-fluoro-5-hydroxy-2-(4-octyloxyphenyl)pyridine and 1.00 g (7.7 mmol) of 1-octanol are subsequently added. After a reaction time of 18 hours at room temperature, the solvent is removed by distillation and the residue is purified by chromatography (silica gel/hexane: ethyl acetate 95:5). Recrystallization from acetonitrile gives 1.38 g of 3-fluoro-5-octyloxy-2-(4-octyloxyphenyl)pyridine.

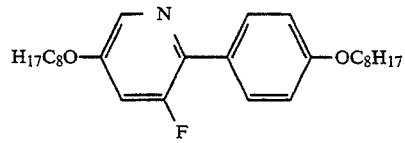

The compound has the phase sequence: X 51.3 (42.5) $S_A$ 50 N 69 I.

EXAMPLE 3

5-decyloxy-2-(4-decyloxyphenyl)-3-fluoropyridine

The synthesis is carried out analogously to Example 2.

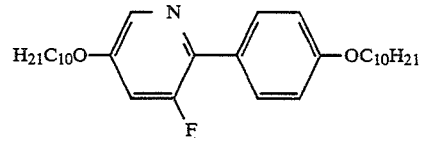

The compound has the phase sequence: X 57 (48) $S_c$ 49 $S_A$ 69 N 70 I.

EXAMPLE 4

3-fluoro-2-(4-octyloxyphenyl)pyridin-5-yl octanoate 1.2 ml (7.1 mmol) of octanoyl chloride are added dropwise at 0° C. to 1.5 g (4.7 mmol) of 3-fluoro-5-hydroxy-2-(4octyloxyphenyl)pyridine in 20 ml of pyridine and the mixture is stirred at 0° C. for 3 hours, subsequently poured into ice-water and filtered and the residue is purified by chromatography (silica gel/hexane: ethyl acetate 9:1) and by recrystallization from acetonitrile, giving 1.34 g of 3-fluoro-2-(4-octyloxyphenyl)pyridin-5-yl octanoate.

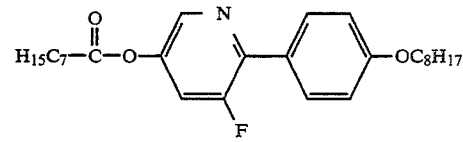

EXAMPLE 5

3-fluoro-2-octyloxy-5-(4-octyloxyphenyl)pyridine 32.0 ml (620.0 mmol) of bromine are added dropwise at 0° C. to 63.7 g (563.2 mmol) of 3-fluoro-2-hydroxypyridine in 700 ml of dimethylformamide. After the mixture has been stirred at room temperature for a further two hours, 800 ml of water are added, and 78 g of $Na_2SO_3$ in 350 ml of water are added dropwise. The mixture is then extracted three times with 400 ml of dichloromethane in each case, and the organic phase is dried over Na₂SO₄ and evaporated to dryness, giving 97.6 g of 5-bromo-3-fluoro-2-hydroxypyridine.

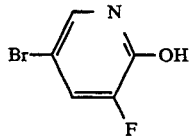

97.6 g (508.0 mmol) of 5-bromo-3-fluoro-2-hydroxypyridine are stirred at 150° C. for 6 hours in 500 ml of phosphorus tribromide. The mixture is subsequently poured into ice water, stirred for 2 hours and extracted three times with dichloromethane, and the organic phase is washed with sodium hydrogencarbonate solution until neutral, dried over sodium sulfate and evaporated to dryness. Chromatographic purification (silica gel/dichloromethane) gives 76.53 g of 2,5-dibromo-3-fluoropyridine.

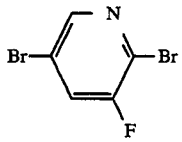

Lithium octanolate (prepared in advance from 13.02 g (100.00 mmol) of 1-octanol and 69 ml (110.00 mmol) of a 1.6 molar n-butyllithium solution in n-hexane at 0° C. in 40 ml of tetrahydrofuran) and 25.49 g (100.00 mmol) of 2,5-dibromo-3-fluoropyridine are refluxed for 7 hours in 40 ml of tetrahydrofuran. The mixture is subsequently partitioned between aqueous sodium chloride solution and ether, and the ether phase is washed twice with aqueous sodium chloride solution, dried over sodium sulfate, filtered and freed from solvent. Chromatographic purification (silica gel/hexane: ethyl acetate 9:1) gives 18.19 g (59.80 mmol) of 5-bromo-3-fluoro-2-octyloxypyridine.

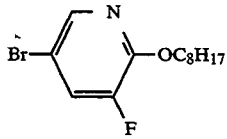

3.00 g (9.86 mmol) of 5-bromo-3-fluoro-2-octyloxypyridine, 2.47 g (9.86 mmol) of 4-octyloxybenzeneboronic acid, 0.11 g (0.10 mmol) of tetrakis(triphenylphosphine)palladium(0) and 2.09 g (19.72 mmol) of sodium carbonate are heated at 80° C. for 3 hours in 90 ml of toluene, 60 ml of ethanol and 30 ml of water. The mixture is subsequently partitioned between aqueous sodium chloride solution and ether and the organic phase is washed with aqueous sodium chloride solution, dried over sodium sulfate, evaporated and purified by chromatography (silica gel/hexane: ethyl acetate 9:1), giving 2.85 g of 3-fluoro-2-octyloxy-5-(4-octyloxyphenyl)-pyridine.

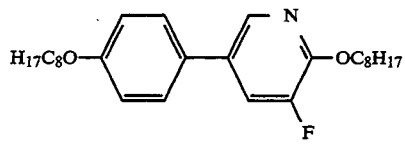

EXAMPLE 6

3-fluoro-5-octyloxy-2-[4-(octyloxyphenyl)phenyl]pyridine

The preparation is carried out analogously to Example 2.

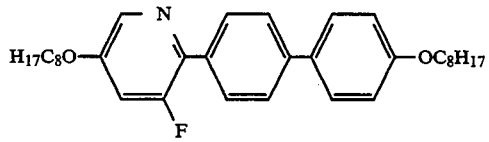

EXAMPLE 7

3-fluoro-2,5-di(4-octyloxyphenyl)pyridine 4.00 g (10.51 mmol) of 5-bromo-3-fluoro-2-(4-octyloxyphenyl)pyridine, 2.63 g (10.51 mmol) of 4-octyloxybenzeneboronic acid, 0.12 g (0.11 mmol) of tetrakis(triphenylphosphine)palladium(0) and 2.23 g (21.02 mmol) of sodium carbonate are heated at 80° C. for 3 hours in 100 ml of toluene, 70 ml of ethanol and 40 ml of water. The mixture is subsequently partitioned between aqueous sodium chloride solution and ether, and the organic phase is washed with aqueous sodium chloride solution, dried over sodium sulfate, evaporated and purified by chromatography (silica gel/dichloromethane), giving 3.72 g of 3-fluoro-2,5-di(4-octyloxyphenyl)pyridine.

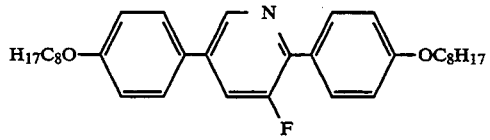

The compound has the phase sequence: X 88 (77.9) S_c 142 S_A 171 N 172 I.

Example 8

3-fluoro-2-octyloxy-5-[4-(4-octyloxyphenyl)phenyl]-pyridine

The preparation is carried out analogously to Example 5.

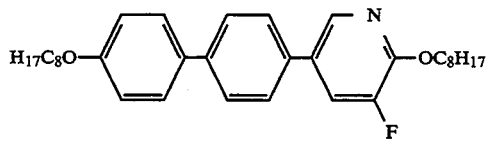

EXAMPLE 9

3-fluoro-2-(4-octyloxyphenyl)pyridin-5-yl trans-4-pentylcyclohexanecarboxylate 0.29 g (0.91 mmol) of 3-fluoro-5-hydroxy-2-(4-octyloxyphenyl)pyridine, 0.19 g (0.91 mmol) of dicyclohexylcarbodiimide, 0.16 g (0.91 mmol) of trans-4-pentylcyclohexanecarboxylic acid and 0.01 g of 4-(N,N-dimethylamino)pyridine are stirred at room temperature for 18 hours in 10 ml of dichloromethane. Filtration, evaporation to dryness, chromatographic purification (silica gel/hexane: ethyl acetate 8:2) and recrystallization from acetonitrile give 0.19 g of 3-fluoro-2-(4-octyloxyphenyl)pyridin-5-yl trans-4-pentylcyclohexanecarboxylate.

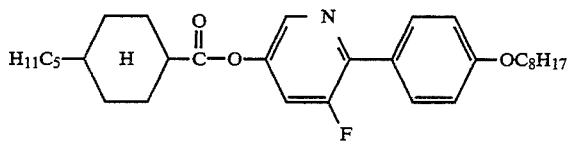

The compound has the phase sequence: X 65.2 (40.2) $S_c$ 63 $S_A$ 129 N 173 I.

EXAMPLE 10

4-(3-fluoro-5-octylpyridin-2-yl)phenyl trans-4-pentylcyclohexanecarboxylate 11.06 g (162.5 mmol) of imidazole in 30 ml of diethylformamide are added dropwise at room temperature to 35.24 g (130.0 mol) of tert-butyl-chlorodiphenylsilane and 11.25 g (65.0 mol) of 4-bromophenol in 150 ml of dimethylformamide. After the reaction mixture has been stirred at room temperature for one hour, it is poured into 1000 ml of 5% strength by weight aqueous sodium hydrogencarbonate solution and extracted twice with 400 ml of dichloromethane, and the organic phase is washed with aqueous sodium chloride solution, dried over sodium sulfate, filtered and evaporated to dryness. Chromatographic purification (silica gel/hexane: ethyl acetate 8:2) gives 23.40 g of 4-bromophenyl tert-butyldiphenylsilyl ether.

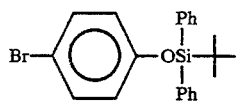

4-bromophenyl tert-butyldiphenylsilyl ether is converted analogously to Example 1 into 4-tert-butyldiphenylsilyloxybenzeneboronic acid.

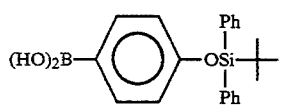

2,5-dibromo-3-fluoropyridine and 4-tert-butyldiphenylsilyloxybenzeneboronic acid are reacted analogously to Example 1 to give 5-bromo-2-(4-tert-butyldiphenylsilyloxyphenyl)-3-fluoropyridine.

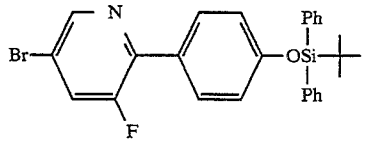

5-bromo-2-(4-tert-butyldiphenylsilyloxyphenyl)-3-fluoropyridine is converted analogously to Example 2 into 2-(4-tert-butyldiphenylsilyloxyphenyl)-3-5-hydroxypyridine.

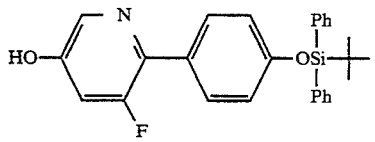

2-(4-tert-butyldiphenylsilyloxyphenyl)-3-fluoro-5-hydroxypyridine and octanol are reacted analogously to Example 2 to give 2-(tert-butyldiphenylsilyloxyphenyl)-3-fluoro-5-octyloxypyridine.

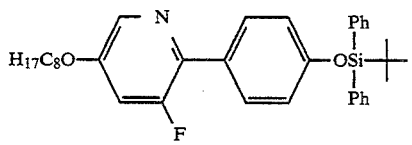

4.30 g (8.00 mmol) of 2-(4-tert-butyldiphenylsilyloxyphenyl)-3-fluoro-5-octyloxypyridine are stirred for 2 hours at room temperature with 16 ml of a 1-molar tetrabutylammonium fluoride solution in tetrahydrofuran in 50 ml of tetrahydrofuran. Aqueous sodium chloride solution is then added, the reaction mixture is extracted with ether, and the ether phase is washed with aqueous sodium chloride solution, dried over sodium sulfate, evaporated to dryness and purified by chromatography (silica gel/hexane: ethyl acetate 8:2), giving 2.16 g of 3-fluoro-2-(4-hydroxyphenyl)-5-octyloxypyridine.

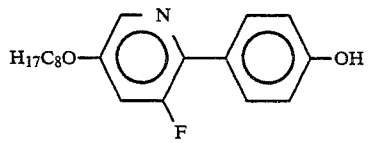

1.11 g (83.50 mmol) of 3-fluoro-2-(4-hydroxyphenyl)-5-octyloxypyridine, 0.72 g (3.50 mmol) of dicyclohexylcarbodiimide, 0.69 g (3.50 mmol) of trans 4-pentylcyclohexanecarboxylic acid and 0.02 g of 4-(N,N-dimethylamino)pyridine are stirred at room temperature for 3 hours in 20 ml of dichloromethane. Filtration, evaporation to dryness, chromatographic purification (silica gel/hexane: ethyl acetate 8:2) and recrystallization from n-hexane give 1.00 g of 4-(3-fluoro-5-octylpyridin-2-yl)phenyl trans-4-pentylcyclohexanecarboxylate.

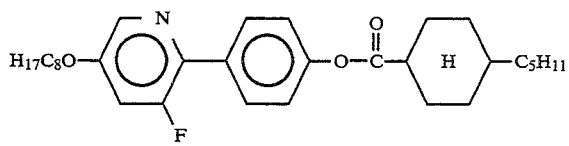

The compound has the phase sequence: X 75 (60) N 169 I.

EXAMPLE 11

3-fluoro-5-octyloxy-2-[4-(trans-4-pentylcyclohexyl)-phenyl]pyridine 4-(trans-4-pentylcyclohexyl)bromobenzene is converted analogously to Example 1 into 4-(trans-4-pentylcyclohexyl)benzeneboronic acid.

4-(trans-4-pentylcyclohexyl)benzeneboronic acid and 2,5-dibromo-3-fluoropyridine are reacted analogously to Example 1 to give 5-bromo-3-fluoro-2-[4-(trans-4-pentylcyclohexyl)phenyl]pyridine.

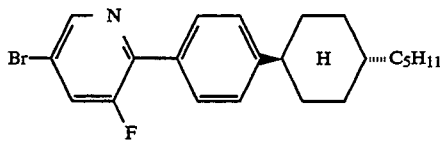

5-bromo-3-fluoro-2-[4-(trans-4-pentylcyclohexyl)-phenyl]pyridine is converted analogously to Example 2 into 3-fluoro-5-hydroxy-2-[4-(trans-4-pentylcyclohexyl)phenyl]pyridine.

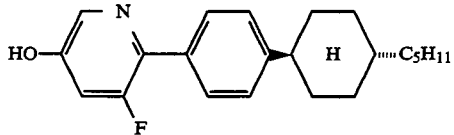

Octanol and 3-fluoro-5-hydroxy-2-[4-(trans-4-pentylcyclohexyl)phenyl]pyridine are reacted analogously to Example 2 to give 3-fluoro-5-octyloxy-2-[4-(trans-4pentylcyclohexyl)phenyl]pyridine.

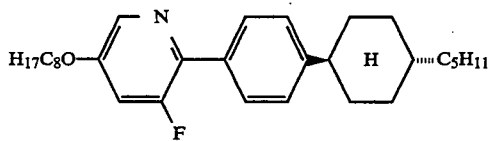

EXAMPLE 12

3-fluoro-2-octyloxy-5-[4-(trans-4-pentylcyclohexyl)-phenyl]pyridine

The preparation is carried out analogously to Example 5.

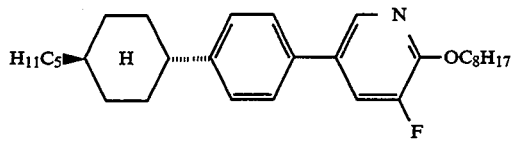

EXAMPLE 13

3-fluoro-5-octyloxy-5-(6-octyloxynaphthalen-2-yl)pyridine

The preparation is carried out analogously to Example 5.

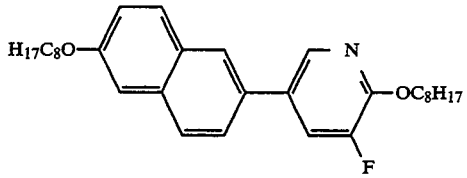

EXAMPLE 14

3-fluoro-5-octyloxy-2-(6-octyloxynaphthalen-2-yl)pyridine

The preparation is carried out analogously to Example 11.

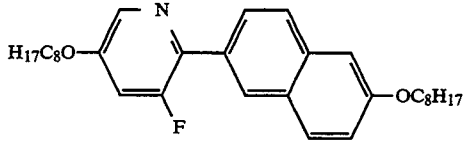

EXAMPLE 15

[(2S,3S)-3-pentyloxiran-2-yl]methyl 3-fluoro-2-(4-octyloxyphenyl)pyridin-5-yl ether 0.44 g (2.55 mmol) of diethyl azodicarboxylate are added dropwise at 0° C. to 0.67 g (2.55 mmol) of triphenylphosphine in 15 ml of tetrahydrofuran, and the mixture is stirred at room temperature for 30 minutes. 0.54 g (1.70 mmol) of 3-fluoro-5-hydroxy-2-(4-octyloxyphenyl)pyridine and 0.25 g (1.70 mmol) of 2-[(2S,3S)-3-pentyloxiranyl]methanol are subsequently added. After a reaction time of 18 hours at room temperature, the solvent is removed by distillation and the residue is purified by chromatography (silica gel/hexane: ethyl acetate 8:2). Recrystallization from hexane: ethyl acetate (8:2) gives 0.28 g of [(2S,3S)-3-pentyloxiran-2-yl]methyl 3-fluoro-2-(4-octyloxyphenyl)pyridin-5-yl ether.

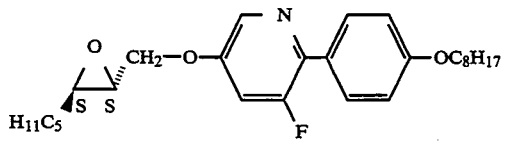

The compound has the phase sequence: X 54.6 (14.5) $S_c$ 53 $S_A$ 65 N 73 I.

EXAMPLE 16

[(2S,3S)-3-pentyloxiran-2-yl]methyl 4-(3-fluoro-5-octyloxypyridin-2-yl)phenyl ether 0.91 g (5.25 mmol) of diethyl azodicarboxylate are added dropwise at 0° C. to 1.37 g (5.25 mmol) of triphenylphosphine in 20 ml of tetrahydrofuran, and the mixture is stirred at 0° C. for 30 minutes. 1.11 g (3.50 mmol) of 3-fluoro-2-(4-hydroxyphenyl)-5-octyloxypyridine and 0.75 g (5.25 mmol) of 2-[(2S,3S)-3-pentyloxiran-2yl]methanol are subsequently added. After a reaction time of 18 hours at room temperature, the solvent is removed by distillation and the residue is purified by chromatography (silica gel/hexane: ethyl acetate 8:2). Recrystallization from hexane gives 0.85 g of [(2S,3S)-3-pentyloxiran-2-yl]methyl 4-(3-fluoro-5-octyloxypyridin-2-yl)phenyl ether.

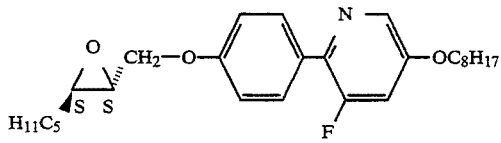

The compound has the phase sequence: X 55 (36) N 68 I.

EXAMPLE 17

[(2S, 3S)-3-pentyloxiran-2-yl]methyl 3-fluoro-2-(4-(trans-4-pentylcyclohexyl)phenyl)pyridin-5-yl ether The preparation is carried out analogously to Example 15.

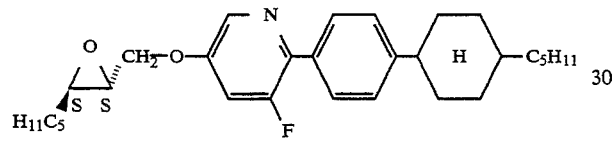

Use Example 1 a) A ferroelectric mixture comprising the components

| | |
|---|---|
| 5-octyloxy-2-(4-hexyloxyphenyl)pyrimidine | 22.8 mol-% |
| 5-octyloxy-2-(4-butyloxyphenyl)pyrimidine | 24.0 mol-% |
| 5-octyloxy-2-(4-decyloxyphenyl)pyrimidine | 19.2 mol-% |
| 5-octyloxy-2-(4-octyloxyphenyl)pyrimidine | 10.5 mol-% |
| 4-(5-decylpyrimidin-2-yl)phenyl trans-4-pentyl-cyclohexanecarboxylate | 13.5 mol-% |
| ((2S,3S)-3-pentyloxiran-2-yl)methyl 3-fluoro-2-(4-octyloxyphenyl)pyridin-5-yl ether | 10.0 mol-% | has the following liquid-crystalline phase ranges: X 3 $S_c$* 89 $S_A$ 94 N* 108 I It has a spontaneous polarization of 9.8 nC/cm$^2$ at a temperature of 20° C. and switches with a response time of 320 μs at a field strength of 10 V/μm.

b) By comparison, a known liquid-crystalline mixture (DE 38 31 226.3) which differs from the abovementioned mixture only in that it does not contain a dope according to the invention, has the following phase ranges: X 9 $S_c$ 84 $S_A$ 93 N 105 I This mixture confirms that ferroelectric mixtures with fast response times can be prepared using the compounds according to the invention.

Use Example 2 a) A mixture which comprises the components

| | |
|---|---|
| 5-octyloxy-2-(4-hexyloxyphenyl)pyrimidine | 16.4 mol-% |
| 5-octyloxy-2-(4-decyloxyphenyl)pyrimidine | 10.9 mol-% |
| 5-decyl-2-(4-hexyloxyphenyl)pyrimidine | 10.6 mol-% |
| 5-octyl-2-(4-(7-cyclopropylheptyloxy)-carbonyloxyphenyl)pyrimidine | 11.0 mol-% |
| 5-(8-cyclopropyloctyloxy)-2-4-(4-trans-pentylcyclohexyl'phenyl)pyrimidine | 12.7 mol-% |
| 4-(5-(8-cyclopropyloctyloxy)pyrimidin-2-yl)phenyl trans-4-pentylcyclohexanecarboxylate | 7.8 mol-% |
| 5-(5-cyclopropylpentyloxy)-2-(4-hexyloxyphenyl)pyrimidine | 11.7 mol-% |
| ((2S,3S)-3-pentyloxiran-2-yl)methyl 4-(3-fluoro-5-octyloxypyridin-2-yl)phenyl ether | 10.0 mol-% | has the following liquid-crystalline phase ranges: X -15 $S_c$* 75 $S_A$ 80 N* 91 I It has a spontaneous polarization of 3.5 nC/cm$^2$ at a temperature of 25° C.

b) By comparison, the liquid-crystalline mixture which differs from the abovementioned mixture only in that it does not contain a dope according to the invention has the following phase ranges: X -13 $S_c$ 65 $S_A$ 70 N 86 I.

Use Examples 1 and 2 additionally confirm that the addition of the compounds according to the invention results in an increase in the $S_c$ phase range.

Use Example 3

A mixture comprises 30 mol-% of 3-fluoro-2-(4-octyloxyphenyl)pyridin-5-yl trans-4-pentylcyclohexanecarboxylate Component A 70 mol-% of 4-ethyl-2-fluoro-4-[2-(trans-4-n-pentylcyclohexyl)ethyl]biphenyl Component B, has a clearing point of 135° C. and crystallizes at −28° C.

By comparison, component B has the following phase transitions:

X 24 $S_B$ (13) N 103.4 I

Addition of component A according to the invention results in a reduction in the crystallization point and an increase in the nematic phase range. This example confirms that the components according to the invention are particularly suitable for broadening the nematic range of liquid crystals. It should furthermore be emphasized that the compound in this example reduces the dielectric anisotropy of the mixture.

Use Example 4

An achiral base mixture which comprises the components

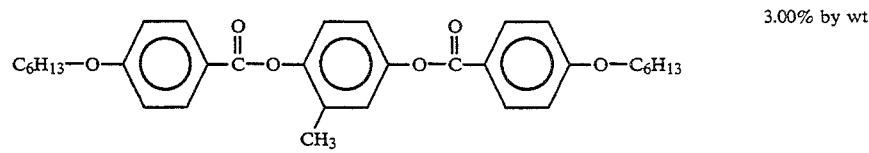

3.00% by wt

-continued

| Structure | Amount |
|---|---|
| C$_6$H$_{13}$—O—[pyrimidine]—[phenyl]—O—C$_6$H$_{13}$ | 3.84% by wt |
| C$_8$H$_{17}$—O—[phenyl]—[pyrimidine]—O—C(=O)—[phenyl]—[cyclohexyl]—H | 12.70% by wt |
| C$_7$H$_{15}$—O—[pyrimidine]—[phenyl]—O—C$_9$H$_{19}$ | 6.40% by wt |
| C$_6$H$_{13}$—O—[pyrimidine]—[phenyl]—O—C$_8$H$_{17}$ | 6.58% by wt |
| C$_8$H$_{17}$—O—[pyrimidine]—[phenyl]—O—C$_6$H$_{13}$ | 7.24% by wt |
| C$_8$H$_{17}$—O—[pyrimidine]—[phenyl]—O—C$_8$H$_{17}$ | 7.77% by wt |
| C$_8$H$_{17}$—O—[phenyl]—[phenyl]—O—C(=O)—[phenyl]—O—C$_4$H$_9$—Si(CH$_3$)$_2$—C$_4$H$_9$ | 5.76% by wt |
| C$_8$H$_{17}$—O—[pyrimidine]—[pyridine]—O—C$_8$H$_{17}$ | 3.98% by wt |
| C$_{10}$H$_{21}$—O—[phenyl]—C(=O)—O—[phenyl]—O—C$_4$H$_9$—Si(CH$_3$)$_2$—C$_4$H$_9$ | 5.29% by wt |
| C$_{10}$H$_{21}$—O—[phenyl]—C=N—N=C(—S—)—[phenyl] (thiadiazole) | 6.64% by wt |
| C$_{10}$H$_{21}$—O—[phenyl]—C(=O)—O—[phenyl]—O—C$_3$H$_6$—CH(CH$_3$)—C$_2$H$_5$ (RAC) | 9.01% by wt |
| C$_8$H$_{17}$—O—[phenyl]—[pyrimidine]—[phenyl]—O—C$_3$H$_7$ | 6.30% by wt |
| C$_8$H$_{17}$—O—[phenyl]—[F-pyridine]—[phenyl]—O—C$_4$H$_9$—Si(CH$_3$)$_2$—C$_4$H$_9$ | 8.12% by wt |

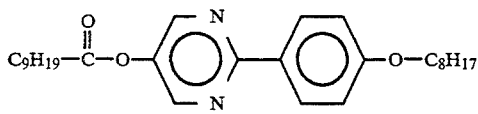

has the following liquid-crystalline phase ranges:

X −21 (−40) S$_c$ 79 S$_A$ 91 N 101 I

Addition of 10% by wt of the substance according to the invention from Example 10 gives a mixture having the phase sequence X −22 (−45) S$_c$ 81 S$_A$ 85 N 106 I It is apparent that the substance according to the invention broadens the nematic phase and raises the S$_A$/S$_c$ transition, and at the same time the melting point is lowered. A broadening in the S$_c$ phase temperature range both to high and low temperatures is of considerable advantage for use, since this broadens the range of the switchable ferroelectric S$_c$* phase (on addition of chiral dopes).

Use Example 5

An achiral base mixture which comprises the components

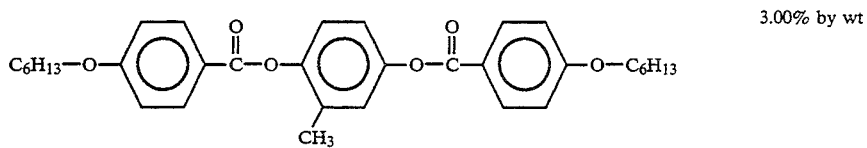
3.00% by wt

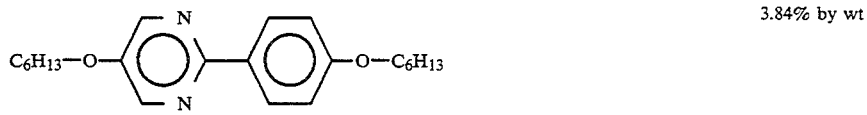
3.84% by wt

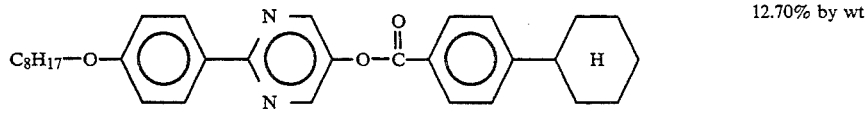
12.70% by wt

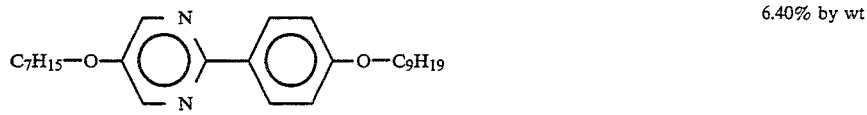
6.40% by wt

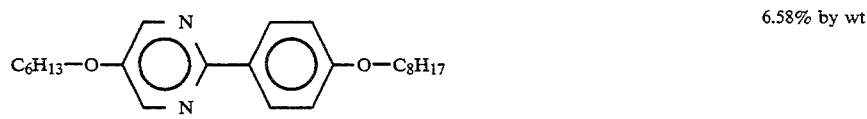
6.58% by wt

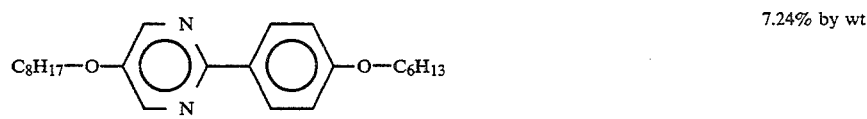
7.24% by wt

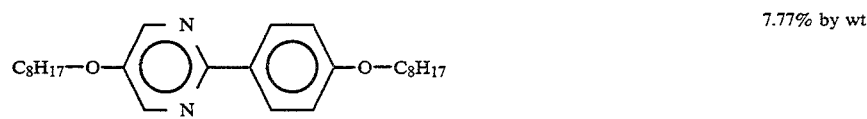
7.77% by wt

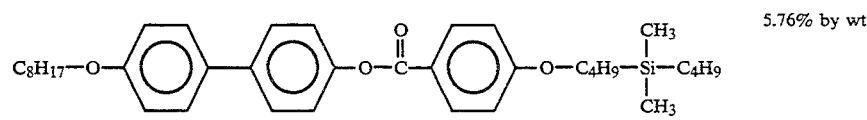
5.76% by wt

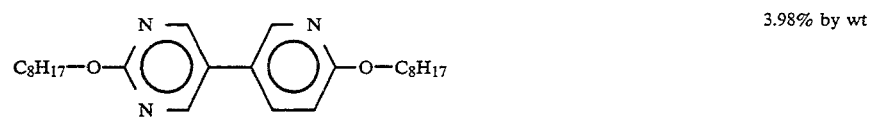
3.98% by wt 7.73% by wt

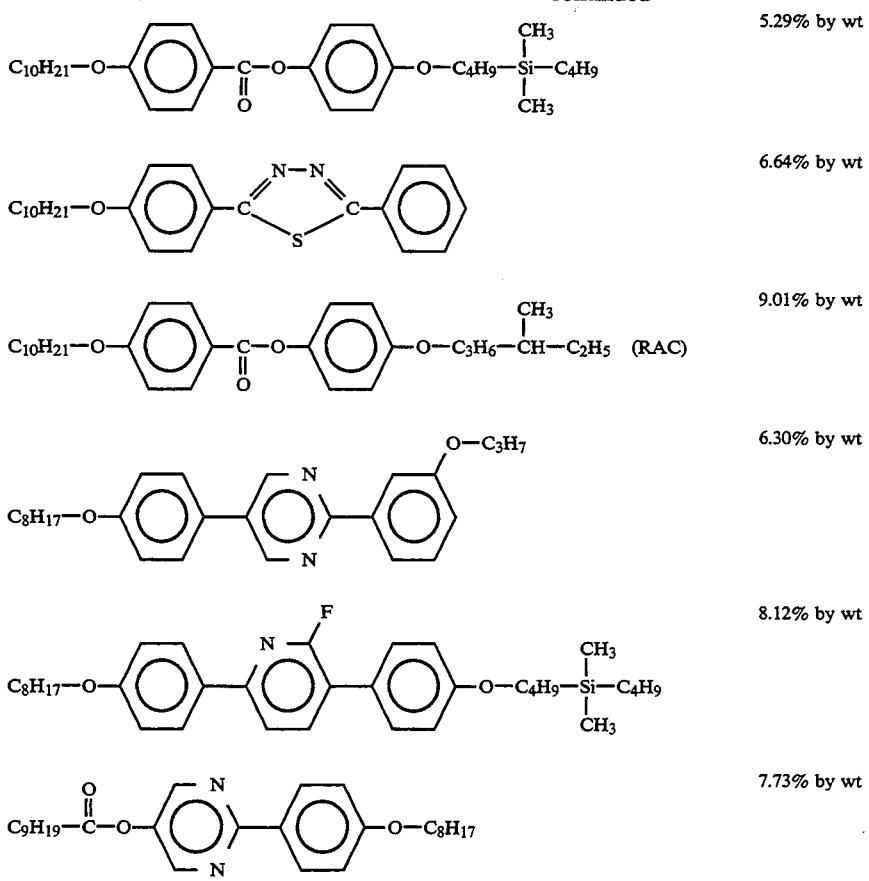

5.29% by wt 6.64% by wt 9.01% by wt 6.30% by wt 8.12% by wt 7.73% by wt has the following liquid-crystalline phase ranges:

X −21 (−40) $S_c$ 79 $S_A$ 91 N 101 I

Addition of 10% by weight of the substance according to the invention from Example No. 16 gives a ferroelectric mixture having the phase sequence X −35 (−41) $S_c$ 76 $S_A$ 85 N 98 I.

The chiral substance hardly changes the liquid-crystalline phase transitions, while the melting point is greatly lowered.

The spontaneous polarization is determined at the following levels:

| T/°C. | Ps/nC |
|---|---|
| 60 | 4.4 |
| 40 | 7.6 |
| 20 | 8.4 |

The substance according to the invention thus enables a variation of the spontaneous polarization and thus of the response speed, without greatly changing the LC phases of the base mixture, while simultaneously lowering the melting point.

We claim:

1. A 3-fluoropyridine compound of the formula (I)

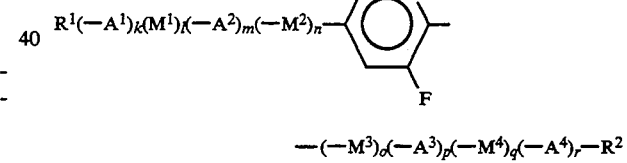

in which the symbols have the following meanings:

$R^1$ and $R^2$, are identical or different and are —H, —F, —Cl, —CN, —CF$_3$, —OCF$_3$, —OCHF$_2$ or straight-chain or branched (with or without an asymmetric carbon atom) alkyl having 1 to 16 carbon atoms, it also being possible for one or two non-adjacent —CH$_2$— groups to be replaced by

—O—, —S—, —CO—, —CO—O—, —O—CO—,

—O—CO—O—, —CH=CH—, —C≡C—,

and it also being possible for one or more hydrogen atoms in the alkyl radical to be substituted by —F, —Cl, or —CN, or are one of the following chiral groups:

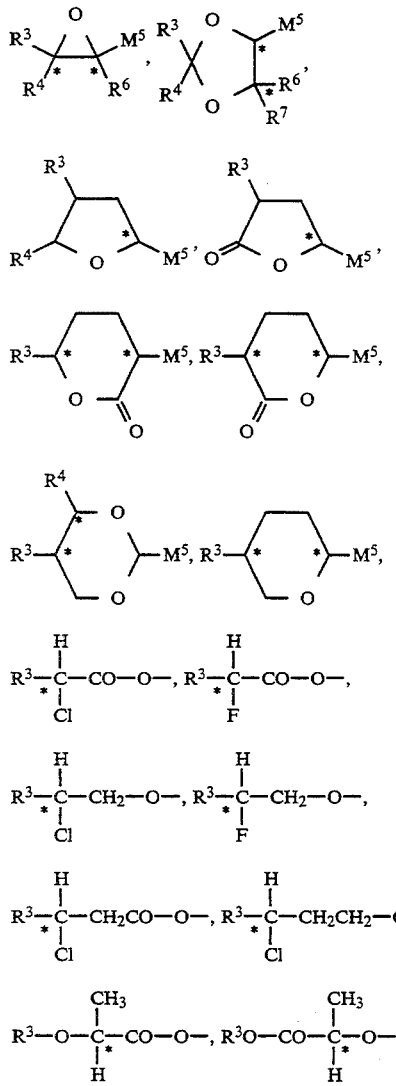

A¹, A², A³ and A⁴ are identical or different and are 1,4-phenylene, pyrazine-2,5-diyl, pyridazine-3,6-diyl, pyridine-2,5-diyl, pyrimidine-2,5-diyl, where one or two hydrogen atoms can be replaced by F, trans-1,4-cyclohexylene, in which one or two hydrogen atoms can in each case be replaced by CN, 1,3,4-thiadiazole-2,5-diyl, 1,3-dioxane-2,5-diyl, naphthalene-2,6-diyl;

M¹, M², M³ and M⁴ are identical or different and are —CO—O—, —O—CO—, —O—CO—O—, —CH₂—O—, —O—CH₂—, —CH₂—CH₂—, or —C≡C—;

R³, R⁴, R⁶ and R⁷ are identical or different and are H or straight-chain or branched alkyl having 1 to 16 carbon atoms, or R³ and R⁴ together are alternatively —(CH₂)₄— or —(CH₂)₅— if bonded as substituents to a dioxolane system;

M⁵ is —CH₂—O—, —CO—O—, —O—CH₂—, —O—CO— or a single bond;

k, l, m, n, o, p, q and r are zero or one, with the proviso that the sum k+m+p+r is less than 4 and greater than zero.

2. A 3-fluoropyridine compound as claimed in claim 1, wherein the symbols in the formula (I) have the following meanings:

R¹ and R² are identical or different and are —H, —F, —CN or straight-chain or branched (with or without an asymmetric carbon atom) alkyl having 1 to 16 carbon atoms, it also being possible for one —CH₂— group to be replaced by

—O—, —S—, —CO—, —CO—O—, —O—CO—,

—O—CO—O—, —CH=CH—, —C≡C—,

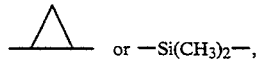 or —Si(CH₃)₂—, or are one of the following chiral groups:

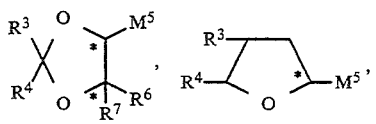

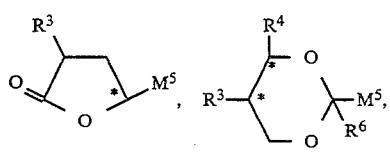

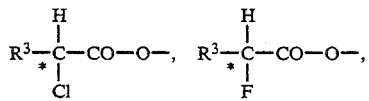

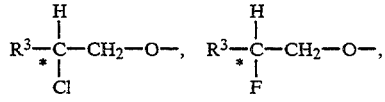

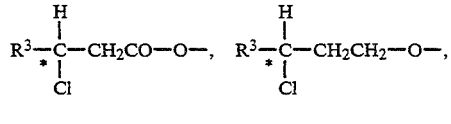

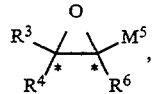

A¹, A², A³ and A⁴ are identical or different and are 1,4-phenylene, pyrazine-2,5-diyl, pyridazine-3,6-diyl, pyridine-2,5-diyl, pyrimidine-2,5-diyl, in which one or two hydrogen atoms can in each case be replaced by F, trans-1,4-cyclohexylene, 1,3,4-thiadiazole-2,5-diyl, 1,3-dioxane-2,5-diyl, naphthalene-2,6-diyl;

M¹, M², M³ and M⁴ are identical or different and are —CO—O—, —O—CO—, —CH₂—O—, —O—CH₂—, —CH₂—CH₂—, or —C≡C—;

R³, R⁴, R⁶ and R⁷ are identical or different and are H or straight-chain or branched alkyl having 1 to 10 carbon atoms, or R³ and R⁴ together are alternatively —(CH₂)₄— or —(CH₂)₅— if bonded as substituents to a dioxolane system;

M⁵ is —CH₂—O—, —CO—O—, —O—CH₂—, —O—CO— or a single bond.

3. A 3-fluoropyridine compound as claimed in claim 1, wherein the symbols in the formula (I) have the following meanings:

$R^1$ and $R^2$ are identical or different and are —H, —F, —CN or straight-chain or branched (with or without an asymmetric carbon atom) alkyl having 1 to 16 carbon atoms, it also being possible for one —CH$_2$— group to be replaced by

—O—, —CO—, —CO—O—, —O—CO—,

—CH=CH—,  or —Si(CH$_3$)$_2$—, or are one of the following chiral groups:

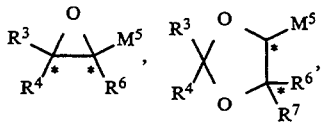 ,  ,

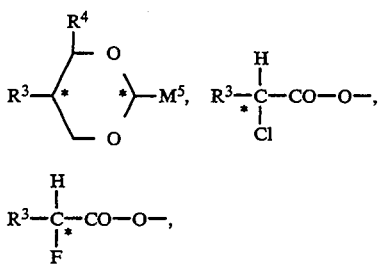

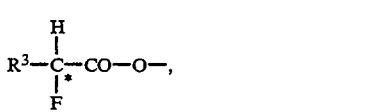

$A^1$, $A^2$, $A^3$ and $A^4$ are identical or different and are 1,4-phenylene, pyrazine-2,5-diyl, pyridazine-3,6-diyl, pyridine-2,5-diyl, pyrimidine-2,5-diyl, in which one or two hydrogen atoms can in each case be replaced by F, trans-1,4-cyclohexylene, 1,3-dioxane-2,5-diyl, naphthalene-2,6-diyl;

$M^1$, $M^2$, $M^3$ and $M^4$ are identical or different and are —CO—O—, —O—CO—, —O—CH$_2$—, —CH$_2$—O—, —CH$_2$—CH$_2$—;

$R^3$, $R^4$, $R^6$ and $R^7$ are identical or different and are H or straight-chain or branched alkyl having 1 to 10 carbon atoms, or $R^3$ and $R^4$ together are alternatively —(CH$_2$)$_4$— or —(CH$_2$)$_5$— if bonded as substituents to a dioxolane system;

$M^5$ is —CH$_2$—O—, —CO—O—, —O—CH$_2$—, —O—CO— or a single bond.

4. A 3-fluoropyridine compound as claimed in claim 1, wherein the symbols in the formula (I) have the following meanings:

$R^1$ and $R^2$ are identical or different and are H or alkyl having 1 to 16 carbon atoms, it also being possible for one —CH$_2$— group to be replaced by —O—, —CO—O— or —O—CO—, or are the chiral group

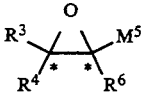

$A^1$, $A^2$, $A^3$ and $A^4$ are identical or different and are 1,4-phenylene, pyrazine-2,5-diyl, pyridazine-3,6-diyl, pyridine-2,5-diyl, pyrimidine-2,5-diyl, in which one or two hydrogen atoms may in each case be replaced by F, trans-1,4-cyclohexylene, 1,3-dioxane-2,5-diyl, naphthalene-2,6-diyl;

$M^1$, $M^2$, $M^3$ and $M^4$ are identical or different and are —CO—O—, —O—CO—, —OCH$_2$—, —CH$_2$—O— or —CH$_2$CH$_2$—;

$R^3$, $R^4$ and $R^6$ are identical or different and are H or a straight-chain alkyl having 1 to 10 carbon atoms; $M^5$ is —CH$_2$—O— or —CO—O—.

5. A liquid-crystal mixture containing at least one compound of the formula (I) as claimed in claim 1.

6. A liquid-crystal mixture as claimed in claim 5, wherein the liquid-crystal mixture is ferroelectric.

7. A liquid-crystal mixture as claimed in claim 5, wherein the liquid-crystal mixture is nematic.

8. A switching and/or display device containing outer plates, electrodes, at least one polarizer, at least one alignment layer and a liquid-crystalline medium, wherein the liquid-crystalline medium is a liquid-crystal mixture as claimed in claim 5.

* * * * *